US012778648B2

(12) United States Patent
Kalyanasundaram et al.

(10) Patent No.: US 12,778,648 B2
(45) Date of Patent: Nov. 3, 2026

(54) ORTHOPEDIC SCREW

(71) Applicant: Indian Institute of Technology Delhi, New Delhi (IN)

(72) Inventors: Dinesh Kalyanasundaram, New Delhi (IN); Arnab Sikidar, New Delhi (IN)

(73) Assignee: INDIAN INSTITUTE OF TECHNOLOGY DELHI, New Dehli (IN)

(*) Notice: Subject to any disclaimer, the term of this patent is extended or adjusted under 35 U.S.C. 154(b) by 789 days.

(21) Appl. No.: 17/294,216

(22) PCT Filed: Nov. 15, 2019

(86) PCT No.: PCT/IN2019/050847

§ 371 (c)(1),
(2) Date: May 14, 2021

(87) PCT Pub. No.: WO2020/100167

PCT Pub. Date: May 22, 2020

(65) Prior Publication Data

US 2022/0000529 A1 Jan. 6, 2022

(30) Foreign Application Priority Data

Nov. 16, 2018 (IN) ............................. 201811043289

(51) Int. Cl.
*A61B 17/86* (2006.01)

(52) U.S. Cl.
CPC ...... *A61B 17/8685* (2013.01); *A61B 17/8605* (2013.01); *A61B 17/8635* (2013.01); *A61B 17/864* (2013.01); *A61B 17/866* (2013.01)

(58) Field of Classification Search
CPC .. A61B 17/864; A61B 17/866; A61B 17/8685
See application file for complete search history.

(56) References Cited

U.S. PATENT DOCUMENTS

| | | | | |
|---|---|---|---|---|
| 3,384,141 | A * | 5/1968 | Kost | F16B 33/006 411/908 |
| 5,209,753 | A * | 5/1993 | Biedermann | A61B 17/8685 606/314 |
| 6,413,260 | B1 * | 7/2002 | Berrevoets | A61B 17/68 606/304 |
| 6,436,142 | B1 * | 8/2002 | Paes | A61F 2/442 623/908 |
| 7,527,611 | B2 * | 5/2009 | Sweeney | A61B 17/7258 604/264 |
| 10,010,361 | B2 * | 7/2018 | Biedermann | A61B 17/686 |
| 11,957,392 | B2 * | 4/2024 | Lee | A61B 17/846 |
| 12,042,195 | B2 * | 7/2024 | Biedermann | A61B 17/866 |

(Continued)

*Primary Examiner* — David W Bates
(74) *Attorney, Agent, or Firm* — Panitch Schwarze Belisario & Nadel LLP

(57) ABSTRACT

An orthopedic screw is provided which includes an outer part having a tip, a head, threads disposed on an outer surface of the outer part between the tip and the head, and a longitudinal cavity with an opening in the head. The orthopedic screw further includes an inner part enclosed by the outer part and is removable from the outer part via the opening of the head. The outer part is made of a material softer than a material of the inner part to ensure shock absorption when the orthopedic screw is in inserted state into a bone of a human body.

9 Claims, 8 Drawing Sheets

(56) References Cited

U.S. PATENT DOCUMENTS

| | | | | |
|---|---|---|---|---|
| 2003/0065332 | A1* | 4/2003 | TenHuisen | A61F 2/0811 606/909 |
| 2004/0267361 | A1* | 12/2004 | Donnelly | A61F 2/0811 623/13.14 |
| 2006/0241593 | A1* | 10/2006 | Sherman | A61B 17/7032 606/264 |
| 2007/0055236 | A1* | 3/2007 | Hudgins | A61F 2/4405 606/278 |
| 2008/0086129 | A1* | 4/2008 | Lindemann | A61B 17/7037 606/86 R |
| 2009/0157123 | A1* | 6/2009 | Appenzeller | A61B 17/8685 606/301 |
| 2009/0157194 | A1* | 6/2009 | Shikinami | A61L 27/446 623/23.72 |
| 2010/0016903 | A1* | 1/2010 | Matityahu | A61B 17/866 606/301 |
| 2010/0036439 | A1* | 2/2010 | Lavi | A61B 17/7225 606/308 |
| 2010/0082071 | A1* | 4/2010 | Moumene | A61B 17/8685 606/318 |
| 2010/0217321 | A1* | 8/2010 | Galley | A61B 17/7068 606/249 |
| 2011/0257689 | A1* | 10/2011 | Fiechter | A61B 17/866 606/301 |
| 2012/0095515 | A1* | 4/2012 | Hamilton | A61B 17/8894 606/104 |
| 2012/0265258 | A1* | 10/2012 | Garvey | A61B 17/8625 606/315 |
| 2012/0330361 | A1* | 12/2012 | Gepstein | A61B 17/7023 606/76 |
| 2014/0005731 | A1* | 1/2014 | Biedermann | A61B 17/686 606/328 |
| 2014/0012336 | A1* | 1/2014 | Biedermann | A61B 17/844 606/328 |
| 2014/0296919 | A1* | 10/2014 | Culbert | A61F 2/44 606/272 |
| 2015/0012048 | A1* | 1/2015 | Huebner | A61B 17/8685 606/304 |
| 2017/0079699 | A1* | 3/2017 | Fallin | A61B 17/725 |
| 2018/0243019 | A1* | 8/2018 | Suh | A61B 17/7001 |
| 2019/0167326 | A1* | 6/2019 | Greenhalgh | A61B 17/8605 |
| 2019/0209220 | A1* | 7/2019 | Lee | A61B 17/863 |
| 2019/0216560 | A1* | 7/2019 | Bono | A61B 34/30 |
| 2020/0085478 | A1* | 3/2020 | McClintock | A61B 17/7059 |
| 2020/0146735 | A1* | 5/2020 | Pepper | A61B 17/866 |
| 2021/0212739 | A1* | 7/2021 | Carrier | A61B 17/683 |
| 2021/0315619 | A1* | 10/2021 | Lacaze | A61B 17/863 |

* cited by examiner

ORTHOPEDIC SCREW

CROSS-REFERENCE TO RELATED APPLICATIONS

This application is a Section 371 of International Application No. PCT/IN2019/050847, filed Nov. 15, 2019, which was published in the Indian language on May 22, 2020 under International Publication No. WO 2020/100167 A1, which claims priority under 35 U.S.C. § 119 (b) to Indian Application No. 201811043289, filed on Nov. 16, 2018, the disclosures of which are incorporated herein by reference in their entireties.

TECHNICAL FIELD

The present subject matter relates, in general, to a screw, in particular, to an orthopedic screw.

BACKGROUND

In general, orthopaedic screws are used to facilitate a fracture fixation of a bone. In one example, the bone is a femoral or a tibia. Such orthopaedic screws are generally meant to provide attachment of complete bone to the bone until healing and integration of the fractured bone.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the figures to reference like features and components. Some implementations of the system(s), in accordance with the present subject matter, are described by way of examples, and with reference to the accompanying figures, in which.

DETAILED DESCRIPTION

Figure 1A:
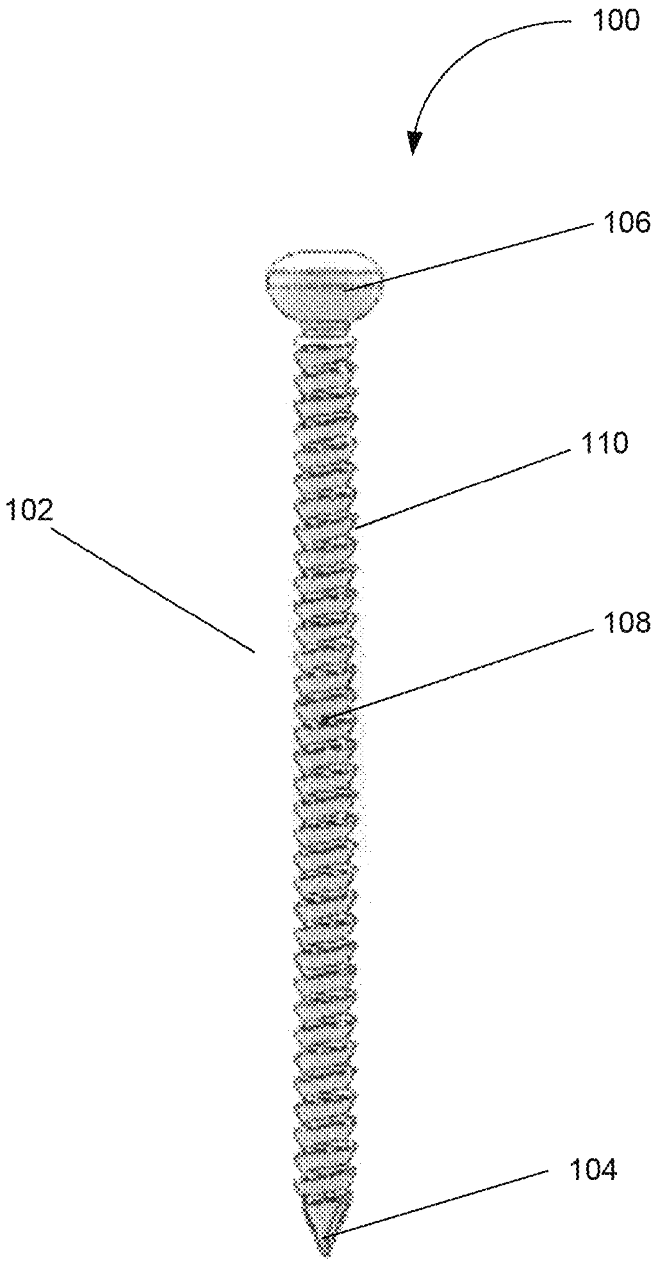
FIG. 1*a* illustrates a front view of an orthopedic screw in accordance with an implementation of the present subject matter.

In bone related surgical procedures, such as repairing fractured bones, a plate or a fastener is attached to a bone for fracture fixation. Such attachment of the plate with the bone is carried out by drilling holes in various bone pieces and the plate or the fastener is then secured to the bone with orthopedic screws having threads. In one example, femur and tibia, which contribute as the largest bones in a human body, when fractured, are treated using fixation of plates with the orthopedic screws.

Such conventional orthopedic screws are generally made of a single material. In general, the single material is metallic. In general, the conventional orthopedic screws cut through the bone tissues during insertion leading to high inflammation. Further the screws are much stiffer than the bone and in certain incidents, the screws have punctured the bone of the patient during an accidental fall. The sharp threads may continue to cause inflammation during routine activities thereby delaying the healing process. Further, upon healing of the bone from facture, the removal of the metallic orthopedic screws causes pain and discomfort to the patient.

To this end, an orthopedic screw is proposed, which is made of a multi-material and improves the healing factor of a bone under fracture in accordance with the implementations of the present subject matter. The orthopedic screw can be understood as a medical device manufactured for insertion into a bone of a human body for assisting in a fracture fixation of the bone.

In an implementation of the present subject matter, the orthopedic screw includes an outer part. The outer part of the orthopedic screw is in direct contact with the bone when the orthopedic screw is inserted into the bone for fracture fixation using a plate or a fastener. The outer part includes a tip, a head, threads disposed on an outer surface of the outer part between the tip and the head, and a longitudinal cavity with an opening in the head. The tip of the outer part is one end of the orthopedic screw and provides an initiating path to the orthopedic screw for insertion in the bone of a human body. The head of the outer part is another end of the orthopedic screw that allows the orthopedic screw to be turned for insertion in the bone of the human body.

Further, the orthopedic screw includes an inner part enclosed by the outer part. In one example, the inner part is removable from the outer part via an opening of the head. The inner part is a reinforcement for structural stability. The inner body is a stiffener that provides the reinforcement and is designed for easy retraction from the orthopedic screw once the bone heals. The outer part is made of a material softer than a material of the inner part. The softer material of the outer part forms an interfacing layer between the reinforcement and the bone of the human body. The interfacing layer between the orthopedic screw and the bone of the human body absorbs shock and compressive loads for avoiding problems of continuous pinching effect or inflammation within the bone or tissues near the bone area. The material of the inner part is rigid and provides stiffness to the orthopedic screw when enclosed in the outer part.

Furthermore, the material of the outer part is either bio-inert or bio-absorbable in nature. After healing of the bone fracture, the inner part can be easily removed or left intact within the bone of the human body with minimally invasive procedures or none respectively. Moreover, the material of the outer part resorbs in the human body to avoid any painful procedure to the patient.

In an implementation of the present subject matter, the material of the outer part is a polymeric or an elastomeric material or a metallic alloy. In one example, the polymeric material is a bioresorbable polymer. The bioresorbable polymer is metabolized by the human body after implantation of the orthopedic screw. In another example, the polymeric material is a bioinert material. Examples of polymeric bioresorbable and bioinert material may include, but is not limited to, polylactide (PLA), polyglycolide (PGA), polyethylenes and copolymers of PLA/PGA. Such polymeric material can be tailored to meet mechanical performance and resorption rates for the orthopedic screw resorbable in nature. Examples of elastomeric material may include, but is not limited to, silicone based materials. Examples of metallic material may include, but is not limited to, magnesium alloys. The polymeric material is light weight and therefore the orthopedic screw of the present subject matter is lightweight. In another example, the elastomeric material may include silicon based materials.

The orthopedic screw of the present subject matter improves the healing factor of the femoral and tibial bone under fracture. Further, the orthopedic screw of the present subject matter facilitates easy recovery with minimal procedure. The self-forming threads of the orthopedic screw do not cut the bone tissues during insertion in the bone and thus reduces inflammation to the bone tissues. The orthopedic screw of the present subject matter may avoid puncture through the bone of the patient having the orthopedic screws inserted, when the patient accidently encounters a fall. Further, the softer threads of the orthopedic screws provide a soothing effect and do not irritate tissues surrounding the bone, in which the orthopedic screws are inserted, during activities such as walking, running or jumping and thereby ensures comfort and reduced inflammation. Further, upon healing of the bone from facture, the removal of the orthopedic screw of the present subject matter causes less or no blood-loss because only the inner part is removed from the bone, which is not directly contacting the tissues and the outer part, which is directly contacting the tissues, is resorbable in the body of the patient.

The implementations of the present subject matter offer the orthopedic screw that provide a design for easy removal of the orthopedic screw post healing. Combination of a soft material and a hard material in the orthopedic screw of the present subject matter provides a shock absorbing affect and a compressive load absorbing affect and the presence of an outer soft material shall avoid problems of continuous pinching effect or inflammation in the bone or tissues surrounding the bone, where the orthopedic screw is inserted. Further, the orthopedic screw of the present subject matter provides a variable stiffness. The stiffness refers to a force required for a unit deflection. In one example, the stiffness can be changed by choosing the same biocompatible material created from different manufacturing processes in order to achieve the variable stiffness. For example, a cold rolled material of same dimensions is less stiff than a hot rolled material.

These and other advantages of the present subject matter would be described in a greater detail in conjunction with FIGS. 1-3 in the following description. The manner in which the orthopedic screw is implemented and used shall be explained in detail with respect to FIGS. 1-3.

It should be noted that the description merely illustrates the principles of the present subject matter. It will thus be appreciated that those skilled in the art will be able to devise various arrangements that, although not explicitly described herein, embody the principles of the present subject matter and are included within its scope. Furthermore, all examples recited herein are intended only to aid the reader in understanding the principles of the present subject matter. Moreover, all statements herein reciting principles, aspects and implementations of the present subject matter, as well as specific examples thereof, are intended to encompass equivalents thereof.

FIG. 1*a* illustrates a front view of an orthopedic screw 100 in accordance with an implementation of the present subject matter. The orthopedic screw 100 can be understood as a medical device manufactured for insertion into a bone (not shown) of a human body (not shown). The orthopedic screw 100 is used to immobilize fractured bone segments (not shown) to aid in a healing process of the bone. The orthopedic screw 100 includes an outer part 102. In one example, the outer part 102 may be made of a softer material. In one example, the softer material is a polymeric material, which is a bioresorbable polymer. Examples of polymeric material may include, but is not limited to, polylactide (PLA), polyglycolide (PGA) and copolymers of PLA/PGA. Other polymeric materials such as Polyether ether ketone (PEEK) or Ultra high density polyethylene (UHMWPE) can also be used. In one example, the outer part 102 is designed based on American Society for Testing and Materials (ASTM) standards for cortical screws (HA-type) and American Society of Mechanical Engineers (ASME) standard for thread-forming. However, the outer part can be designed based on other standards suggested for orthopedic screws. Further, the outer part 102 of the orthopedic screw 100 includes a tip 104, a head 106, and threads 108 disposed on an outer surface 110 of the outer part 102 of the orthopedic screw 100. The tip 104 is a pointed end of the orthopedic screw 100. The head 106 is another end of the orthopedic screw 100. In one example, the head 106 may be round. In another example, other shapes of the head 106 are also possible. The thread 108 is a helical structure that is used to convert between rotational and linear movement. In other words, the thread 108 is a ridge wrapped around a cylinder or cone in the form of a helix, with the former being called a straight thread and the latter called a tapered thread.

The threads 108 of the orthopedic screw 100 are formed in such a manner that the orthopedic screw 100 is self-forming. The self-forming of the orthopedic screw 100 is an ability to form a thread in a material into which the orthopedic screw 100 is inserted.

Further, the outer part 102 includes a longitudinal cavity (not shown in FIG. 1*a*). The longitudinal cavity is formed to accommodate an inner part (not shown in FIG. 1*a*) of the orthopedic screw 100. In one example, the inner part corresponds to the shape of the longitudinal cavity. The longitudinal cavity has a cross-section corresponding to a cross-section of the inner part.

Figure 1B:
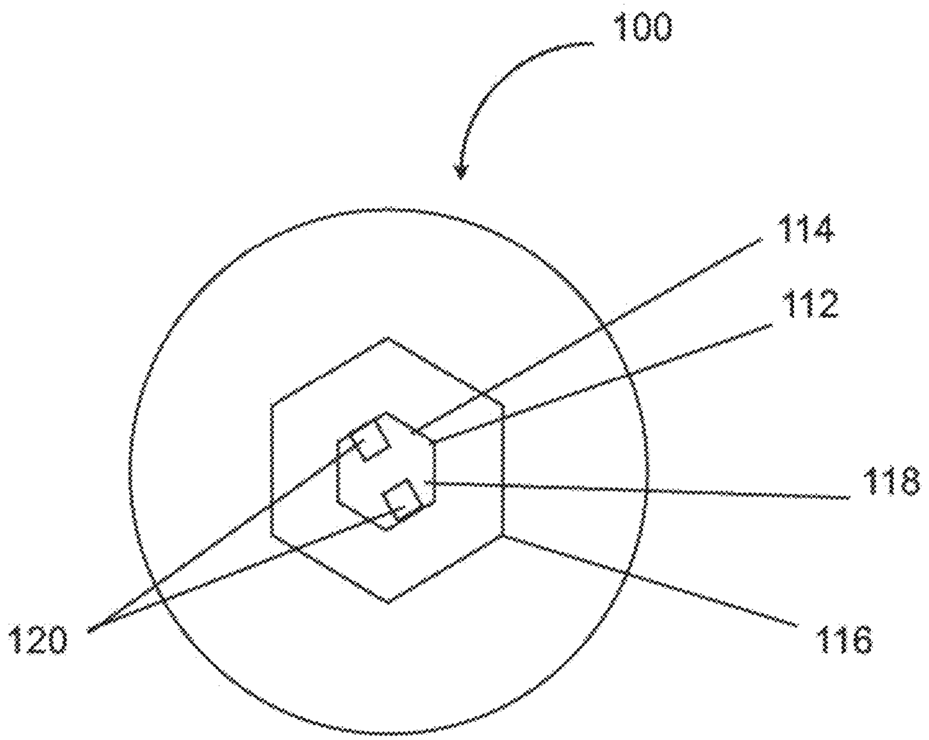
FIG. 1*b* illustrates a top view of an orthopedic screw in accordance with an implementation of the present subject matter.
Figure 1C:
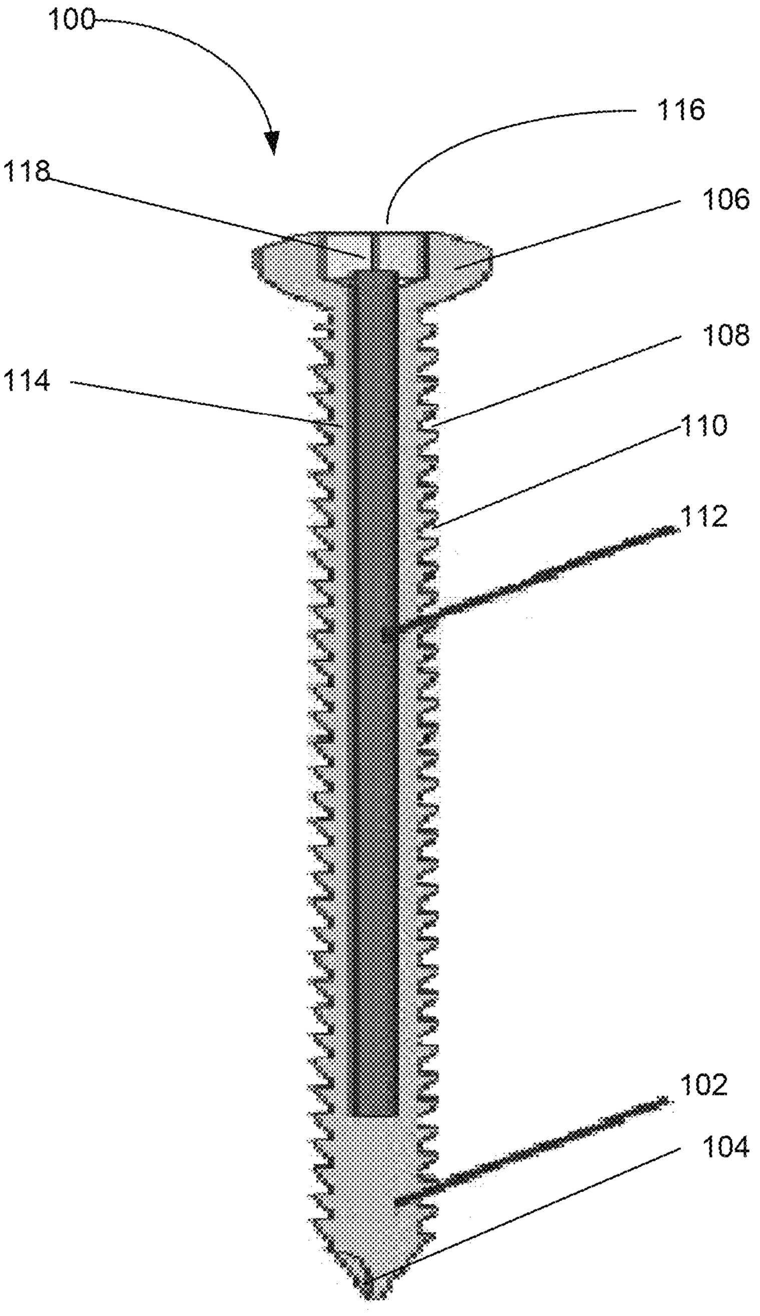
FIG. 1*c* illustrates a sectional view of an orthopedic screw in accordance with an implementation of the present subject matter.

FIG. 1*b* illustrates a top view of the orthopedic screw 100 in accordance with an implementation of the present subject matter. The inner part 112 is shown in an inserted state, in which the inner part 112 is enclosed by the longitudinal cavity 114 of the outer part 102 of the orthopedic screw 100. The longitudinal cavity 114 can be clearly seen in FIG. 1*c*, which illustrates a sectional view of the orthopedic screw 100 in accordance with an implementation of the present subject matter. Hereinafter, FIGS. 1*a*, 1*b* and 1*c* are explained in conjunction with each other. In one example, the longitudinal cavity 114 may be regular or irregular polygonal in cross-section. In another example, the longitudinal cavity 114 either tapered or non-tapered. The longitudinal cavity 114 comprises an opening 116 in the head 106 of the outer part 102. The inner part 112 can be inserted into the longitudinal cavity 114 of the outer part 102 via the opening 116 in the head 106 of the outer part 102 of the orthopedic screw 100. In one example of the present subject matter, the inner part 112 can be removed from the longitudinal cavity 114 of the outer part 102 via the opening 116 in the head 106 of the outer part 102 of the orthopedic screw 100. The insertion and removal of the inner part 112 to and from the longitudinal cavity 114 of the outer part 102 via the opening 116 in the head 106 of the outer part 102 of the orthopedic screw 100 is an easy procedure. To enable such procedure, the inner part 112 includes a head 118 at a top surface thereof. The head 118 includes slots 120 on the top surface for insertion and removal of the inner part 112 to and from the longitudinal cavity 114 of the outer part 102. In one example, number of slot 120 may be multiple. In another example, the head 118 may be magnetic and the inner part 112 can be removed from the longitudinal cavity 114 of the outer part 102 via the opening for tightening head 116 in the head 106 of the outer part 102 of the orthopedic screw 100 by applying a magnetic field. Further, the tightening head 116 may be polygonal so as to fix an Allen key (not shown) for screwing the orthopedic screw 100 into the bone of the human body.

In an example of the present subject matter, the outer part 102 is made of the material softer than a material of the inner part 112. The softer material of the outer part 102 absorbs shock and compressive loads for avoiding problems of continuous pinching effect or inflammation within the bone or tissues (not shown) near a bone area (not shown). The material of the inner part 112 is rigid and provides stiffness to the orthopedic screw 100 when enclosed in the outer part 102.

In one example, the inner part 112 is made of a reinforcing material. In another example, the reinforcing material is a metallic material. In yet another example, the metallic material is a bio-compatible alloy. One example of biocompatible alloy is Ti—Al—V alloy. Other biocompatible metallic materials such as $Ti_6Al_4V$ Grade 5 Titanium alloy can also be used as the material of the inner part 112. The inner part 112 is a variable stiffener that provides a reinforcement and is designed for easy retraction from the orthopedic screw 100 once the bone heals.

Figure 3A:
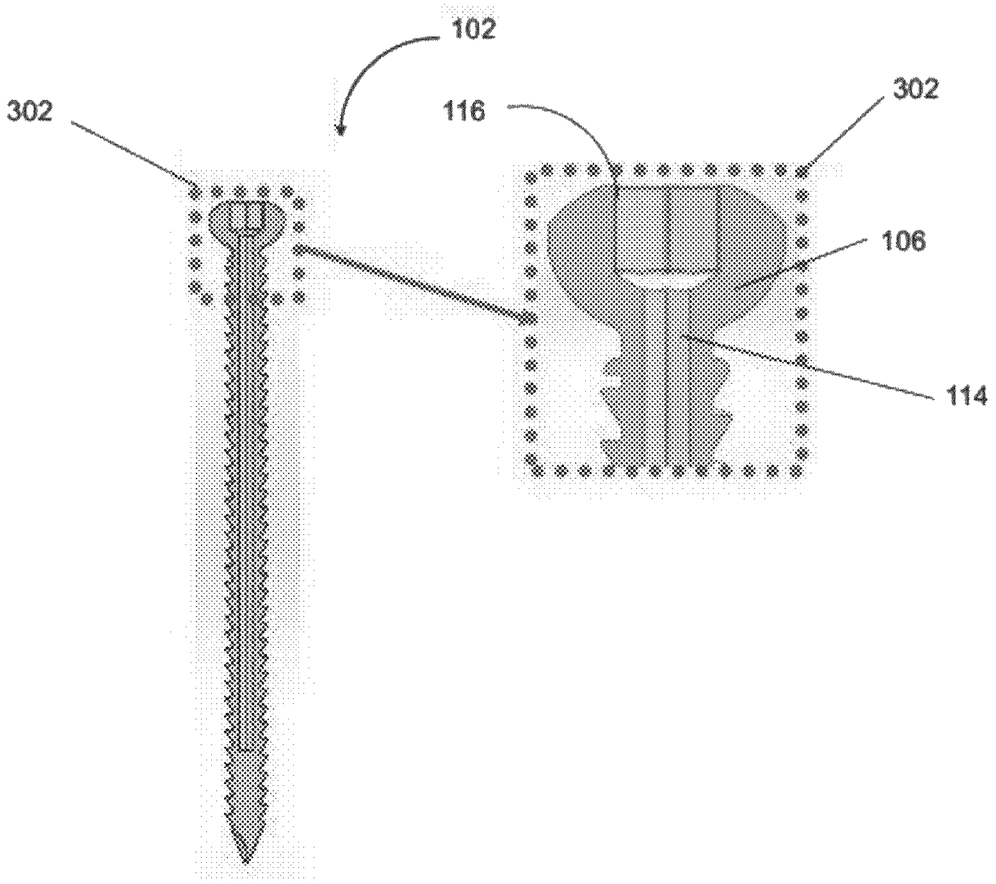
FIG. 3*a* illustrates a sectional view of an outer part with a magnified end portion in accordance with an implementation of the present subject matter.

Further, the outer part 102 is shown in detail in FIG. 3*a*, which illustrates a sectional view of the outer part 102 with a magnified end portion 302 in accordance with an implementation of the present subject matter. The magnified end portion 302 shows the opening 116 in the top surface of the head 106 of the outer part 102, through which the inner part 112 can be inserted and removed from the outer part 102.

Figure 3B:
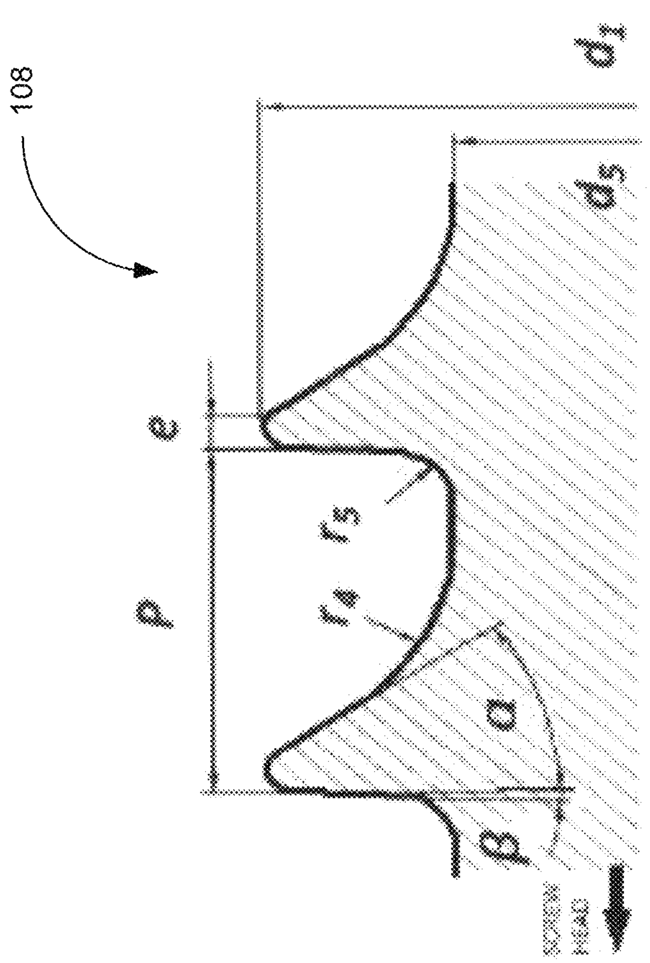
FIG. 3*b* illustrates a schematic representation of a threading specification of a thread of an outer part in accordance with an implementation of the present subject matter.

Returning to FIG. 1*c*, the specification of the threads 108 is shown in detail in FIG. 3*b*. FIG. 3*b* illustrates a schematic representation of a threading specification of the threads 108 of the outer part 102 in accordance with an implementation of the present subject matter. The outer part 102 is defined as a cortical screw of HA 4.5 as per ASTM standards (ASTM F543-17) and self-forming thread as per ASME 18.6.4. The cortical screw of HA type includes shallow threads.

Returning to FIG. 1*c*, the inner part 112 and the outer part 102 form a single assembly, which can be inserted into the bone for fracture fixation.

Figure 1D:
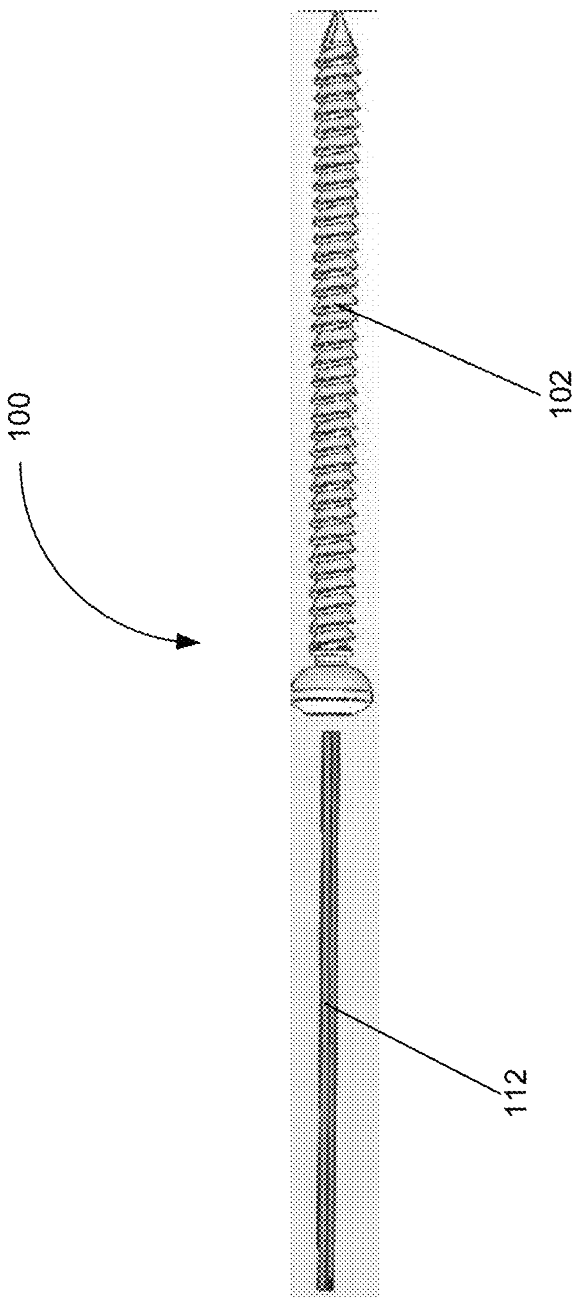
FIG. 1*d* illustrates an exploded view of an orthopedic screw in accordance with an implementation of the present subject matter.

FIG. 1*d* illustrates an exploded view of the orthopedic screw 100 in accordance with an implementation of the present subject matter. In non-assembled state of the orthopedic screw 100, the inner part 112 is shown outside the outer part 102. The inner part 112 is insertable and removable outside the outer part 102. The inner part 112 is shown in detail in FIGS. 2*a* and 2*b*.

Figure 2A:
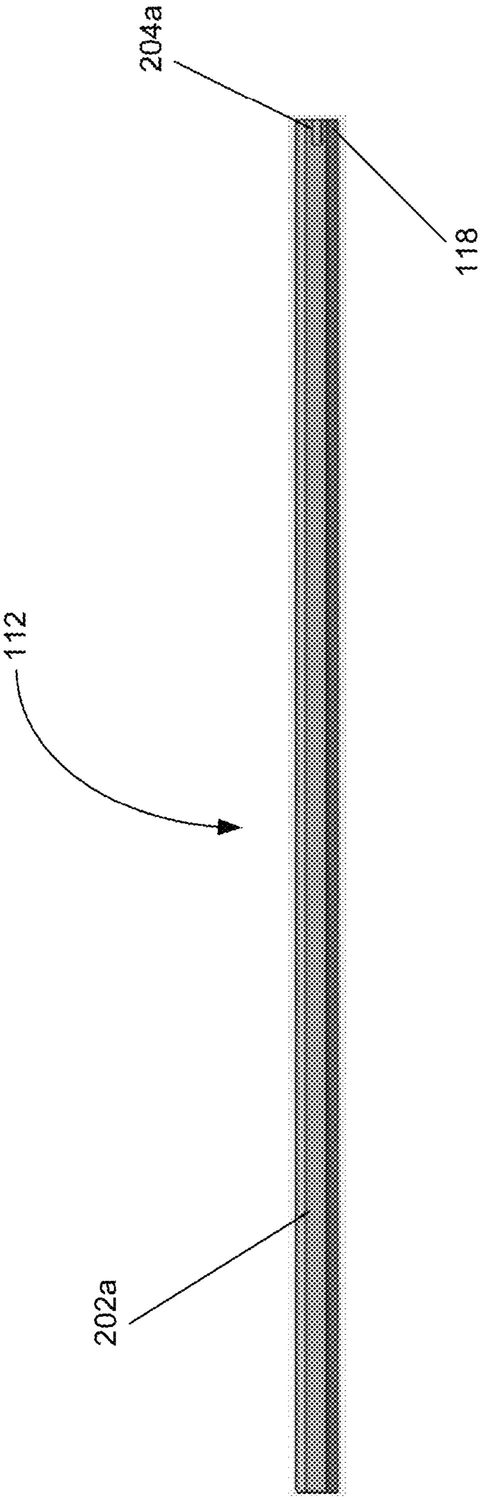
FIG. 2*a* illustrates a front view of an inner part in accordance with an implementation of the present subject matter.
Figure 2B:
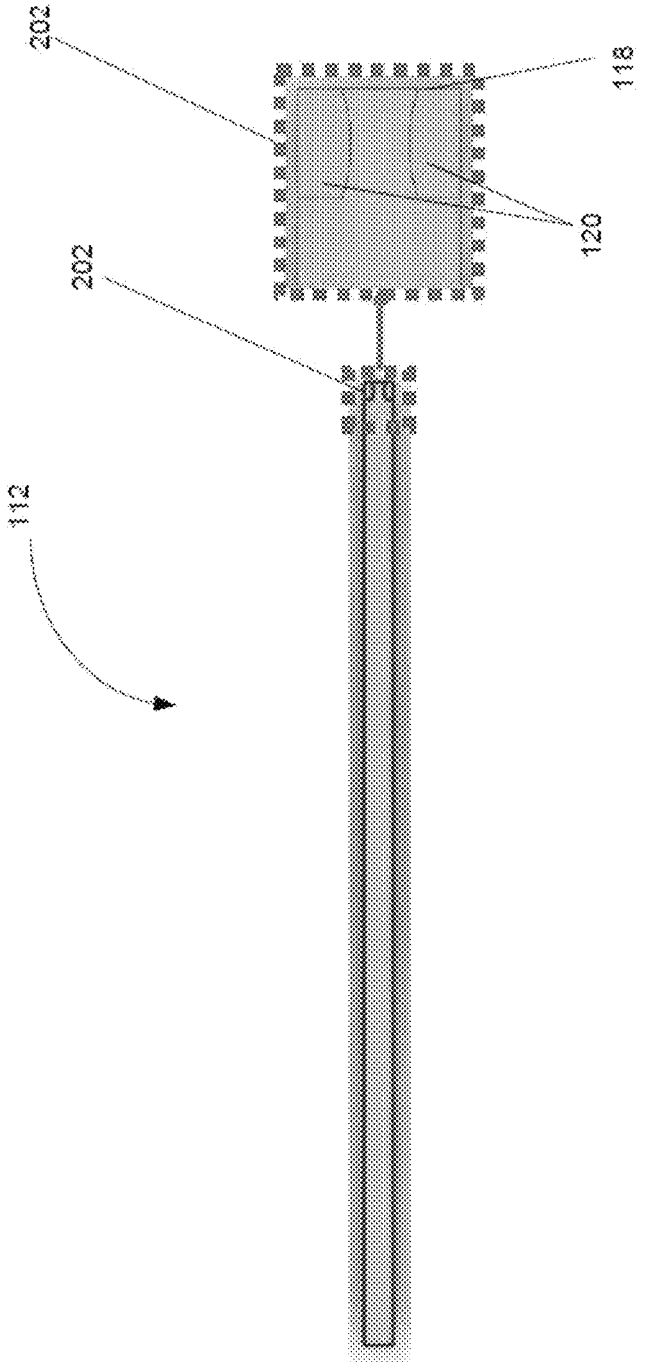
FIG. 2*b* illustrates a sectional view of an inner part with a magnified end portion in accordance with an implementation of the present subject matter.

FIG. 2*a* illustrates a front view of an inner part 112 in accordance with an implementation of the present subject matter and FIG. 2*b* illustrates a sectional view of an inner part 112 with a magnified end portion 202 in accordance with an implementation of the present subject matter. FIGS. 2*a* and 2*b* are further explained in conjunction with each other. The inner part 112 incudes a reinforcing rod 202*a*. In one example, the longitudinal cavity 114 has a cross-section corresponding to match a cross-section of the reinforcing rod 202*a*. In one example, the reinforced rod can either be tapered or non-tapered along the length or follow any profile.

In one example, the cross-section of the reinforcing rod 202*a* is of any shape corresponding a regular or irregular polygon. The reinforcing rod 202*a* acts as axial stiffener, the properties of which can be varied to match the stiffness of an end-user bone requirements (not shown). Further, a top end 204*a* of the reinforcing rod 202*a* includes the head 118. The head 118 includes the slot 120 on the top surface for removal of the inner part 112 from the outer part 102 by using a specified tool (not shown). In one example, the specified tool may be forceps. In one example, the head 118 may be magnetically removed from the outer part 102 of the orthopedic screw 100.

In one example, the tightening head 116 has a cross-sectional shape of a hexagon. The hexagonal cross-section of the tightening head 116 allows fixing of the Allen key over the head 118 of inner part 112, which can be further screwed to insert the orthopedic screw 100 into the bone of the human body. In another example, the tightening head 116 has a cross-sectional shape of a square and a key (not shown) corresponding to the square cross-section can be used to insert the orthopedic screw 100 into the bone of the human body.

In yet another example, the inner part 112 may have any regular or irregular polygonal cross-section. In one further example, the inner part 112 has a circular cross-section. The inner part 112 is a variable stiffener that provides a reinforcement and is designed for easy retraction from the orthopedic screw 100 once the bone has healed. The variable stiffener can also be left intact inside once the bone is healed. This will eliminate the need for invasive measures for retraction and will undermine the discomfort to the patient.

The reinforcing rod 202*a* acts as a support for the outer part 102 in transmission of a torsional force while screwing the orthopedic screw 100 inside the bone due to the hexagonal cross-section. The reinforcing rod 202*a* also provides a better structural rigidity and improves the flexural strength of the outer part 102.

Although examples for the present disclosure have been described in language specific to structural features and/or methods, it should be understood that the appended claims are not necessarily limited to the specific features or methods described. Rather, the specific features and methods are disclosed and explained as examples of the present disclosure.

We claim:

1. An orthopedic screw (100) comprising:

an outer part (102), the outer part (102) being a solid continuous tubular structure with an unslitted wall thereof, and having a tip (104), a head (106), threads (108) disposed on an outer surface (110) of the outer part (102) between the tip (104) and the head (106), and a longitudinal cavity (114) extending distally from the head (106) towards the tip (104); and an inner part (112) configured to be positioned in an axially stationary manner, and enclosed within the longitudinal cavity (114) of the outer part (102), such that the inner part (112) does not protrude from the outer part (102), the inner part (112) configured to be removable from the longitudinal cavity (114) of the outer part (102), the inner part (112) comprising a reinforcing rod (202*a*) with a proximal end, a distal end, and a magnetic head at the proximal end for insertion and removal of the inner part (112) from the outer part (102), wherein the inner part (112) is configured to provide support to the outer part (102) via the reinforcing rod (202*a*) filling the longitudinal cavity (114), wherein the outer part (102) is configured to prevent the inner part (112) from directly contacting tissue proximal to the outer surface (110) when the inner part (112) is positioned within the longitudinal cavity (114), wherein the outer part (102) is made of a material softer than a material of the inner part, wherein the material of the outer part (102) forms an interfacing layer configured to separate the inner part (112) and a bone, and wherein the material of the outer part (102) is a biocompatible and bio-absorbable polymeric material.

2. The orthopedic screw (100) as claimed in claim 1, wherein the longitudinal cavity (114) has a cross-section corresponding to a cross-section of the inner part (112).

3. The orthopedic screw (100) as claimed in claim 1, wherein the threads (108) are formed such that the orthopedic screw (100) is self-forming.

4. The orthopedic screw (100) as claimed in claim 1, wherein the threads (108) are formed such that the orthopedic screw (100) is self-cutting.

5. The orthopedic screw (100) as claimed in claim 1, wherein the inner part (112) is a reinforcement for structural stability.

6. The orthopedic screw (100) as claimed in claim 5, wherein the inner part (112) is made of a metallic material.

7. The orthopedic screw (100) as claimed in claim 6, wherein the metallic material is a bio-compatible alloy.

8. The orthopedic screw (100) as claimed in claim 5, wherein the reinforcement has a cross-section of a regular or irregular polygon.

9. The orthopedic screw (100) as claimed in claim 5, wherein the inner part (112) has a circular cross-section.

* * * * *